Figure 1:
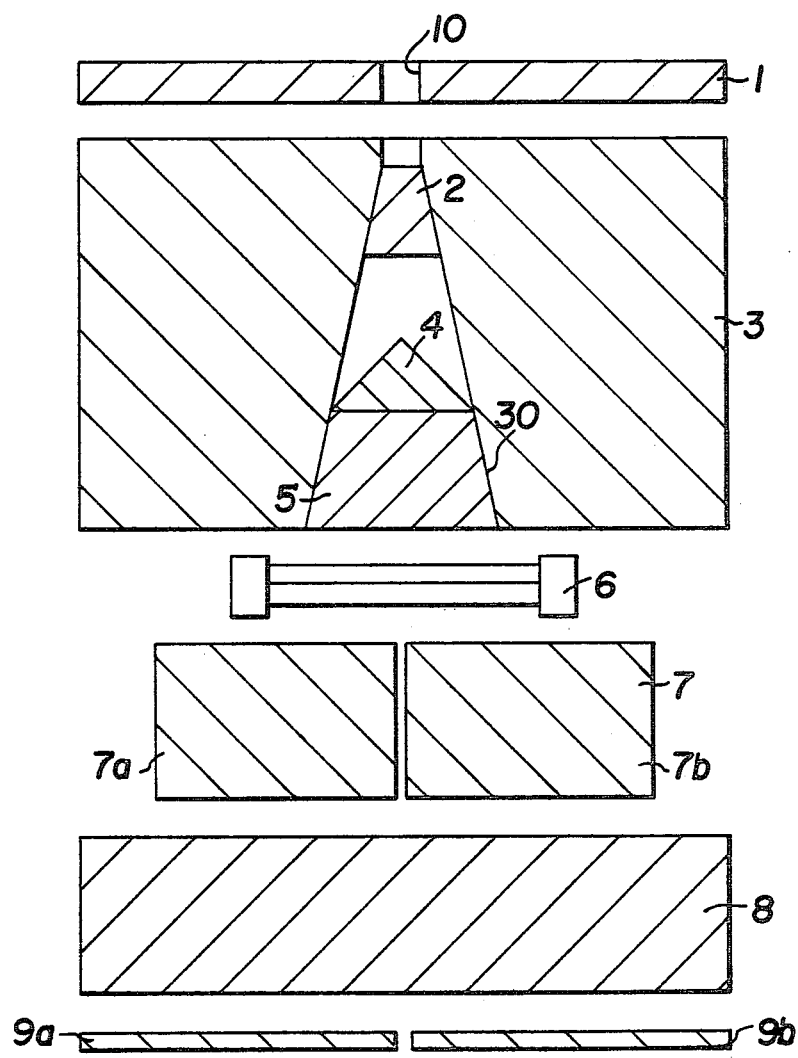

United States Patent [19]

McHugh et al.

[11] 4,198,570
[45] Apr. 15, 1980

[54] UNITARY SELF SHIELDED, SELF FILTERED AND FLATTENED BREMSSTRAHLUNG PHOTON SOURCE ASSEMBLY FOR RADIOTHERAPY USE

[75] Inventors: Philip McHugh; William R. Brown, both of Ottawa; Peter W. Brown, Almonte, all of Canada

[73] Assignee: Atomic Energy of Canada Limited, Canada

[21] Appl. No.: 894,453

[22] Filed: Apr. 7, 1978

[30] Foreign Application Priority Data

Jan. 9, 1978 [CA] Canada ................................. 294533

[51] Int. Cl.² ............................................... H05G 3/00
[52] U.S. Cl. .................................. 250/503; 250/505; 250/510
[58] Field of Search ............... 250/493, 503, 505, 510, 250/396 R, 398, 492 R

[56] References Cited

U.S. PATENT DOCUMENTS

| 3,767,931 | 10/1973 | Williams | 250/503 |
| 3,969,629 | 7/1976 | McIntyre | 250/503 |
| 4,121,109 | 10/1978 | Taumann et al. | 250/505 |

*Primary Examiner*—Bruce C. Anderson
*Attorney, Agent, or Firm*—Beveridge, DeGrandi, Kline & Lunsford

[57] ABSTRACT

A photon source filter and primary collimator arrangement wherein the source and filter are within the boundaries of the primary collimator and together form a unitary assembly which may be fixed relative to the impinging electron beam or may be removable from the same. The assembly may consist of low and high atomic number elements or compounds.

5 Claims, 3 Drawing Figures

UNITARY SELF SHIELDED, SELF FILTERED AND FLATTENED BREMSSTRAHLUNG PHOTON SOURCE ASSEMBLY FOR RADIOTHERAPY USE

This invention relates to a unitary self shielded, self filtered and flattened Bremsstrahlung photon source assembly. This invention has particular but not exclusive use with high energy sources such as produced by Van de Graff machines, betatrons, synchrotrons and other electron accelerators. The invention can be usefully applied to cancer therapy apparatus.

X-ray or Bremsstrahlong (braking radiation) is produced when an electron is slowed down by mutual attraction between its negative charge and the positive nuclear charge on the atoms of the absorbing material.

The spectrum of this radiation is continuous in energy with a maximum corresponding to the initial energy of the incident electrons. The energy of the photon emission falls off with polar angle from the initial direction of motion of the electrons.

The maximum size of the x-ray beam is limited by a shielding member call the primary definer. This shielding member allows the x-ray beam to pass through a truncated conical aperture.

Low atomic number filter materials will preferentially reduce the low energy component of photon beams above 10 million electron volts. Such filters are sometimes used to produce more penetrating radiation beams in radiotherapy.

The polar intensity distribution of high energy x-rays are characterized by a lobe or peak in the direction of the incident electron beam. Accelerators used for radiotherapy employ conical filters which flatten the central portion of the lobe to produce a therapeutically useful beam. These are called beam flatteners or beam flattening filters.

Accelerators used for radiotherapy employ transmission ionization chambers which are used to control the position of the beam on the target and the radiation output of the machine.

In conventional radiotherapy accelerators, these components are aligned in series as follows—target, primary definer, beam flattener or beam flattening filter and the transmission ionization chamber.

The principal feature of this invention is the integration of two or more of these components into a single assembly by utilizing the space in the aperture of the primary definer.

It is a feature of one object of the invention to provide a unitary self shielded Bremsstrahlung photon source assembly.

It is a feature of another object of the invention to provide a self filtered Bremsstrahlung photon source assembly.

It is a feature of yet another object of the invention to provide a Bremsstrahlung photon source assembly with an improved flattened field.

In accordance with the foregoing objects, there is provided a Bremsstrahlung photon source assembly having a plurality of elements disposed substantially on a common axis, said elements comprising a head shielding member having a first aperture therethrough for receiving and passing a beam of high energy electrons, a primary collimator disposed adjacent said head shielding member having a second aperture designed such that it can contain a target member at the top end and diverges away from the target at the lower end, a target member disposed in the said second aperture, said target member producing Bremsstrahlung radiation upon bombardment by said high energy electrons, a filter having divergent sides, said filter being disposed within said second aperture adjacent to the larger dimension thereof, an ionization chamber disposed adjacent the said primary collimator and, first and second collimator leaf or block assemblies each of which comprises a pair of separable leaves which define an adjustable slot therebetween said slots being disposed substantially symmetrically about said common axis, each pair of leaves being rotatable about said common axis.

Figure 2:
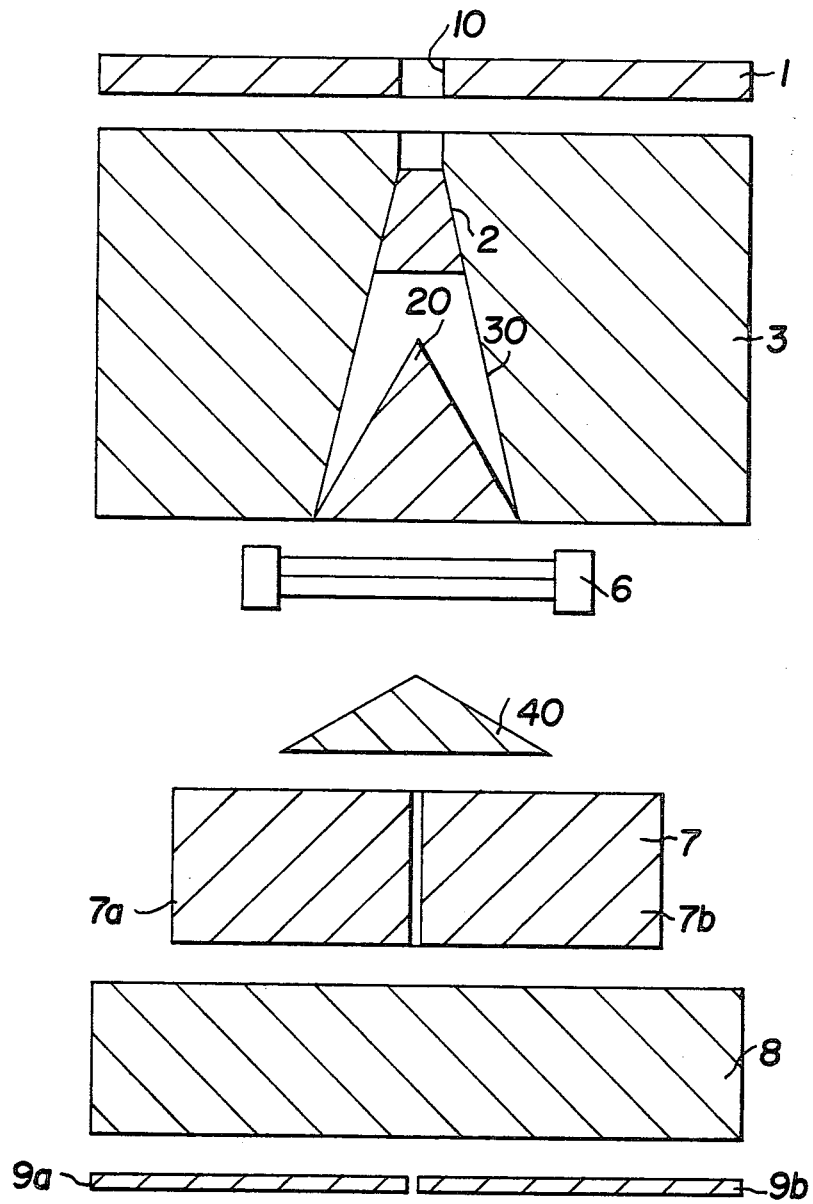
Figure 3:
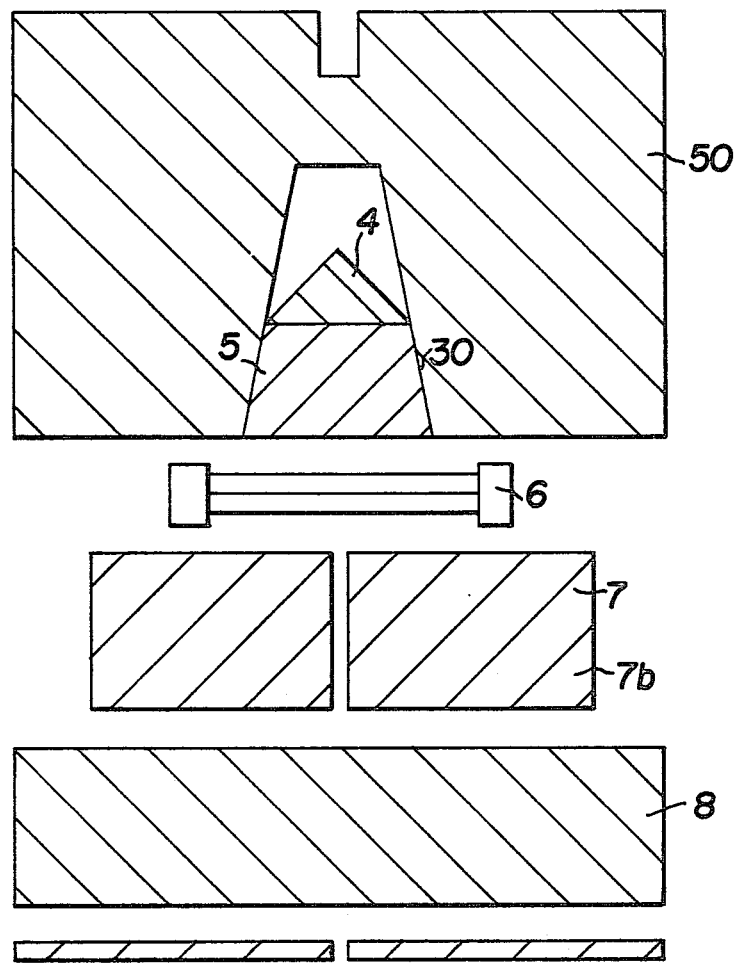

A preferred embodiment of the invention will be described with reference to the following drawings in which FIGS. 1, 2, 3 are cross-sectional views of 3 varients of the invention in which like numbers identify similar parts.

The output end of a high energy electron source (not shown) for example, an accelerator, emits electrons which pass through a head shield 1 having a window 10 extending therethrough. The high energy electrons impinge on a target 2 wherein the electrons are decelerated in the coulomb fields of the atomic nuclei to produce Bremsstrahlung radiation in the form of x-rays. The target 2 is surrounded by a primary collimator 3 which includes a divergent passage 30. The x-ray beam passes through the beam flattener 4 and energy filter 5 which are inside the divergent passage 30. The x-rays then proceed out of the primary collimator 3, through an ion chamber 6 and collimator leaves 7, 8, 9 respectively. Leaves 7 are constituted by relatively and laterally separable portions 7a and 7b, while leaves 9 are similarly constituted by portions 9a and 9b. The plane of separation of corresponding separable leaves may be generally perpendicular to the plane of separation of leaves 7 and 9 although each of the leaves 7, 8, and 9 are individually rotatable about the longitudinal axis of the assembly. The assembly thus described may have a total height, from top to bottom, of about 50 cms.

Referring now to FIG. 2, the assembly shown is in most respects the same as in FIG. 1, but with some changes now to be discussed. The conical flattener 4 and the filter 5 in FIG. 2 may be combined into a flattening filter 20 of conical configuration. If greater flattening is required, an additional flattening filter 40 may be employed.

Referring now to FIG. 3, the shielding member 1, the target 2 and the primary definer 3 are combined into one single member 50.

In all three embodiments the utilization of the space within the primary definer allows the use of filters or beam flatteners of long axial dimension.

The invention thus described provides for a radiator (target) and filter disposed within the confines of the primary collimator and together form a unitary assembly which may be fixed relative to the impinging electron beam or may be removable from same or may be rotatable around same.

The assembly may consist of low and high atomic number elements or compounds and may be incorporated into an accelerator type cancer therapy machine.

With suitable choice of materials, the invention can result in a higher average energy photon beam and consequently better characteristics for radiotherapy and can result in simplified shielding of the x-ray target.

Other embodiments falling within the terms of the appended claims will occur to those skilled in the art.

The embodiments of the invention in which an exclusive property or privilege is claimed are defined as follows.

1. A Bremsstrahlung photon source assembly having a plurality of elements disposed substantially on a common axis, said elements comprising:
   (i) A head shielding member having a first aperture therethrough for receiving and passing a beam of high energy electrons,
   (ii) A primary collimator disposed adjacent said head shielding member and having a second aperture therein which diverges away from said head shielding member,
   (iii) A target member disposed in the second aperture adjacent to the smallest dimension of same, said target member producing Bremsstrahlung radiation upon bombardment by said high energy electrons,
   (iv) A filter disposed within said second aperture adjacent the larger dimension of same for filtering said beam,
   (v) An ion chamber disposed adjacent the said primary collimator, and,
   (vi) First and second collimator leaf assemblies each of which comprises a pair of separable leaves which define an adjustable slot therebetween said slots being disposed substantially symmetrically about said common axis, each pair of separable leaves being rotatable about said common axis.

2. A Bremsstrahlung source as in claim 1 further including a beam flattening member disposed between the target and the filter.

3. A Bremsstrahlung source as in claim 1 wherein said beam flattening member and said filter are integrally formed of like or dissimilar materials.

4. A Bremsstrahlung photon source as in claim 2 including an additional beam flattening member disposed between said source assembly and the first collimator leaf assembly.

5. A Bremsstrahlung photon source as in claim 1 wherein the head shielding member, the primary collimator and the target are integrally formed.

* * * * *